US011117843B2

(12) United States Patent
Lahougue et al.

(10) Patent No.: US 11,117,843 B2
(45) Date of Patent: Sep. 14, 2021

(54) METHOD FOR CONVERTING A GAS COMPRISING CARBON MONOXIDE INTO METHANE BY MEANS OF A CATALYTIC MATERIAL CONTAINING PRASEODYMIUM AND NICKEL ON ALUMINA

(71) Applicants: ENGIE, Courbevoie (FR); ENERCAT, Ploemeur (FR)

(72) Inventors: Arnaud Lahougue, Courbevoie (FR);
Emmanuel Rohart, Courbevoie (FR);
Gaëlle Gicquel, Courbevoie (FR);
Sandra Capela, Courbevoie (FR);
Yilmaz Kara, Courbevoie (FR);
Stéphane Fortin, Courbevoie (FR);
Myriam De Saint Jean, Courbevoie (FR)

( * ) Notice: Subject to any disclaimer, the term of this patent is extended or adjusted under 35 U.S.C. 154(b) by 0 days.

(21) Appl. No.: 16/757,511

(22) PCT Filed: Oct. 22, 2018

(86) PCT No.: PCT/FR2018/052619
§ 371 (c)(1),
(2) Date: Apr. 20, 2020

(87) PCT Pub. No.: WO2019/077288
PCT Pub. Date: Apr. 25, 2019

(65) Prior Publication Data
US 2020/0239381 A1 Jul. 30, 2020

(30) Foreign Application Priority Data
Oct. 20, 2017 (FR) ...................... 1759927

(51) Int. Cl.
*C07C 1/04* (2006.01)
*B01J 8/18* (2006.01)
*B01J 21/04* (2006.01)
*B01J 23/10* (2006.01)
*B01J 23/755* (2006.01)
*B01J 35/02* (2006.01)
*B01J 35/10* (2006.01)
*B01J 37/02* (2006.01)
*B01J 37/08* (2006.01)
*B01J 37/16* (2006.01)

(52) U.S. Cl.
CPC ........... *C07C 1/0485* (2013.01); *B01J 8/1827* (2013.01); *B01J 8/1836* (2013.01); *B01J 21/04* (2013.01); *B01J 23/10* (2013.01); *B01J 23/755* (2013.01); *B01J 35/026* (2013.01); *B01J 35/1014* (2013.01); *B01J 35/1019* (2013.01); *B01J 35/1061* (2013.01); *B01J 37/0221* (2013.01); *B01J 37/082* (2013.01); *B01J 37/16* (2013.01); *C07C 1/041* (2013.01); *C07C 1/0435* (2013.01); *B01J 2208/00132* (2013.01); *C07C 2521/04* (2013.01); *C07C 2523/10* (2013.01); *C07C 2523/755* (2013.01)

(58) Field of Classification Search
CPC ............ B01J 2523/31; B01J 2523/3718; B01J 2523/847; B01J 35/1019; B01J 35/1061; C07C 1/0435; C07C 9/04; C07C 1/12; C10G 2/32
See application file for complete search history.

(56) References Cited

U.S. PATENT DOCUMENTS

| 4,539,016 A | 9/1985 | Flockenhaus et al. |
| 2015/0360209 A1* | 12/2015 | Teunissen ............ B01J 37/0009 518/715 |

FOREIGN PATENT DOCUMENTS

| CN | 103933994 A | 7/2014 |
| CN | 103933994 B | 12/2015 |
| FR | 2600556 A1 | 12/1987 |
| GB | 1152008 A | 5/1969 |
| WO | 00/16901 A1 | 3/2000 |

OTHER PUBLICATIONS

She et al (Shiyou Huagong (1989), 18(12), 824-9 Abstract only).*
ISR; European Patent Office; NL; dated Feb. 7, 2019.
Shin-Ichiro Fujita et al: Mechanisms of Mathanation of Carbon Dioxide and Carbon Monoxide Over Nickel/Alumina Catalysts, Oct. 7, 1993.
Database WPI; Week 201468, Thompson Scientific, London; XP002788712; Dec. 2, 2015.
Ahmad Waqar et al; "Synthesis of Lanthanide Series (La, Ce, Pr, Eu & Gd) Promoted Ni/[Gamma]—A1203Catalysts for Methanation of C02AT Low Temperature Under Atmospheric Pressure" Jun. 27, 2017.
Wan Azelee Wan Abu Bakar et al: "Nickel Oxide Based Supported Catalysts for the In-Siteu Reactions of Mathanation and Desulfurization in the Removal Od Sour Gases From Simulated Natural Gas." Nov. 11, 2008.
Hezhi Liu et al: "Effect of CE02 Addition on Ni/AL203 Catalysts for Methanation of Carbon Dioxide With Hydrogen" Journal of Natural Gas Chemistry; Nov. 1, 2012.
Mohd Hasmizam Razali: "CO2/H2 Mathanation on Nickel Oxide Based Catalysts Doped With Lanthanide Series" Jan. 1, 2005.

* cited by examiner

*Primary Examiner* — Jafar F Parsa
(74) *Attorney, Agent, or Firm* — PatShegen IP; Moshe Pinchas

(57) ABSTRACT

The invention relates to a method for converting a gas into methane ($CH_4$) which includes:
a step of activating a catalytic material including praseodymium oxide ($Pr_6O_{11}$) associated with nickel oxide (NiO) and alumina ($Al_2O_3$), the respective proportions of which are, relative to the total mass of these three compounds:
$Pr_6O_{11}$: 1 wt % to 20 wt %,
NiO: 1 wt % to 20 wt %, and
$Al_2O_3$: 60 to 98 wt %; and
a step of passing a gas including at least one carbon monoxide (CO) over the activated catalytic material.

19 Claims, 2 Drawing Sheets

METHOD FOR CONVERTING A GAS COMPRISING CARBON MONOXIDE INTO METHANE BY MEANS OF A CATALYTIC MATERIAL CONTAINING PRASEODYMIUM AND NICKEL ON ALUMINA

TECHNICAL FIELD OF THE INVENTION

The present invention concerns a method and a device for converting a gas into methane. It applies to the field of the conversion of carbon monoxide (CO) in a gas mixture rich in hydrogen, possibly in the presence of carbon dioxide (CO2), into a mixture rich in methane (CH4), in a larger range of temperatures and, in particular, at low temperatures.

STATE OF THE ART

Catalytic materials that contain nickel oxide and alumina are known. The nickel oxide content is generally high and varies, depending on the methods, from 20% to 50%. The catalytic performance levels of these materials are sometimes judged insufficient, especially when the temperatures of the method are low, for example below 300° C. In addition, the thermodynamics show that the lower the reaction temperature, the higher the methane conversion rate and the lower the level of excess reagents. As the commercially available catalysts are mainly active at temperatures higher than 300° C., their conversion rate is limited by the thermodynamics. Lastly, the high nickel content has an adverse effect on the cost price of these materials, and in some cases on how the disposal of the used loads is handled. The document "Synthesis of lanthanide series (La, Ce, Pr, Eu & Gd) promoted Ni/[gamma]—Al2O3 catalysts for methanation of CO2 at low temperature under atmospheric pressure" by Ahmad Waqar et al., Catalysts Communications, Elsevier, Amsterdam, NL, vol. 100, Jun. 27 2017, pages 121-126, XP085145534, ISSN: 1566-7367, DOI: 10.1016/J.Catcom. 2017.06.044 is known.

The document "Nickel Oxide Based Supported Catalysts for the In-Situ Reactions of Methanation and Desulfurization in the removal of Sour Gases from Simulated Natural Gas" by Wan Azelee Wan Abu Bakar et al., Catalysis Letters, Kluwer Academic Publishers, NE, vol. 128, no. 1-2, Nov. 11 2008, pages 127-136, XP019671959, ISSN: 1572-879X is also known.

The document "Effect of CeO2 addition on Ni/Al2O3 catalysts for methanation of carbon dioxide with hydrogen" by Hezhi Liu et al., Journal of Natural Gas Chemistry, vol. 21, no. 7, Nov. 1, 2012, pages 703-707, XP055276014, US, CN ISSN: 1003-9953 (11) 60422-2 is also known.

Document WO 00/16901 is also known.

Lastly, the document "CO2/H2 Methanation on Nickel Oxide based Catalysts dopes with Lanthanide Series" by Mohd Hasmizan Razali, Malaysian Journal of Analytical Sciences, vol. 9, no. 3, Jan. 1, 2005 is known.

Each of these documents is restricted solely to converting carbon dioxide into methane.

SUBJECT OF THE INVENTION

The present invention aims to remedy all or part of these drawbacks. To this end, according to a first aspect, the present invention relates to a method for converting a gas into methane (CH4), which comprises:
a step of activating a catalytic material including praseodymium oxide (Pr6O11) associated with nickel oxide (NiO) and alumina (Al2O3), the respective proportions of which are, relative to the total mass of these three compounds:
Pr6O11: 1 wt % to 20 wt %,
NiO: 1 wt % to 20 wt %, and
Al2O3: 60 wt % to 98 wt %; and
a step of passing a gas including at least carbon monoxide (CO) over the activated catalytic material.

The inventors have discovered that the choice of the combination of compounds of the catalytic material and the respective content of each of these elements, (Pr6O11, NiO and Al2O3), provide a good performance/durability/cost compromise when this catalytic material is used for converting carbon monoxide (CO) in a gas mixture rich in hydrogen (H2), possibly in the presence of carbon dioxide (CO2), into a gas mixture rich in methane (CH4), for example mainly containing CO, CO2 and H2, and offering high performance in converting the group consisting of CO and CO2 at a low temperature, for example at temperatures below 300° C.

This catalytic material has a broader operating temperature range than the catalytic materials previously known. Because of thermodynamic laws, the conversion of CO and CO2 is increased, especially at low temperatures.

The catalytic material in the strict sense can be in powdery form, in which the mean size of the grains varies from 1 to 100 µm, in the form of beads of 100 µm to 1 mm, preferably between 200 and 800 µm and, even more preferably, between 200 and 600 µm.

It is noted that the catalyst formed by activating the catalytic material that is the subject of the invention can be used in different forms other than beads, for example powder, foam (metal or ceramic), coated on ceramic (cordierite, mullite, etc.) or metallic substrates, or ceramic filters, extruded with different geometries (single-lobe, three-lobe, etc.), pellets. In some embodiments, the gas passing over the activated catalytic material also comprises carbon dioxide (CO2).

In some embodiments, the proportion of carbon monoxide in the gas reaching the activated catalytic material is higher than five percent by volume in dry gas.

In some embodiments, during the gas passage step, a gas mixture is passed that mainly contains CO, CO2 and H2, with an H2 content higher than that of CO and CO2.

In some embodiments, during the gas passage step, the mean temperature of the catalytic layer is below 300° C. It is noted that, even though the fluidized bed makes increased exchanges possible, a slight temperature peak linked to very rapid kinetics remains near the reaction front.

In some embodiments, the method comprises a step of shaping the catalytic material into beads with a mean size of between 100 and 1000 µm.

In some embodiments, before the activation step, the catalytic material has respective proportions, relative to the total mass of these three compounds, of:
Pr6O11: 3 wt % to 15 wt %,
NiO: 3 wt % to 15 wt %, and
Al2O3: 70 wt % to 94 wt %.

In some embodiments, before the activation step, the catalytic material has respective proportions, relative to the total mass of these three compounds, of:
Pr6O11: 5 wt % to 12 wt %,
NiO: 6 wt % to 12 wt %, and
Al2O3: 76 wt % to 88 wt %.

In some embodiments, the alumina has a mesoporosity corresponding to a median diameter of the pores, determined by Hg intrusion porosimetry, of between 3 and 50 nm.

In some embodiments, the alumina has a gamma structure.

In some embodiments, the catalytic material's specific surface area SStel is between 50 and 300 m²/g.

In some embodiments, the catalytic material's specific surface area SStel is between 100 and 250 m²/g.

The performance/durability/cost compromise is therefore further improved.

In some embodiments, the step of activating the catalytic material comprises heat treatment in the presence of reducing agents.

In some embodiments, the step of activating the catalytic material in the presence of reducing agents is performed in a temperature range of 300-500° C., and preferably 400-500° C.

In some embodiments, the method also comprises a step of the solubilization of salt precursors of nickel and praseodymium, separately or in a mixture;

a step of the surface deposition of metal salts on a carrier based on alumina (Al2O3); and a step of thermal decomposition in an atmosphere comprising oxygen and in a temperature range of 350-500° C., for a period of between one hour and four hours.

In some embodiments, the method comprises, before the gas passage step, a step of constituting the gas comprising at least one of the following steps:

pyrolysis of hydrocarbon materials;

pyro-gasification of hydrocarbon materials;

gasification of hydrocarbon materials;

co-electrolysis of CO2/H2O;

Water-Gas-Shift; and

Reverse Water-Gas-Shift.

These different steps provide a gas comprising carbon monoxide.

In some embodiments, during the step of passing the gas over the catalytic material, the gas goes through a catalytic layer of activated catalytic material.

In some embodiments, the catalytic layer is preferably a bed fluidized by the passage of the gas through the catalytic material.

In some embodiments, at least one heat exchange tube is immersed in the catalytic layer.

Each heat exchange tube makes it possible to control the temperature of the methanation reaction. The particular catalytic material of the invention enables an efficient conversion at an average temperature of less than 300° C., favorable to both the speed of the reaction and its yield.

According to a second aspect, the present invention relates to a method for preparing a catalyst, which comprises:

a step of the solubilization of salt precursors of nickel and praseodymium, separately or in a mixture;

a step of the surface deposition of metal salts on a carrier based on alumina (Al2O3);

a step of thermal decomposition in an atmosphere comprising oxygen; and a step of activating the material obtained by heat treatment in the presence of reducing agents.

According to a third aspect, the present invention relates to a device for converting a gas into methane (CH4), which comprises:

a catalytic layer obtained by activating a catalytic material including praseodymium oxide (Pr6O11) associated with nickel oxide (NiO) and alumina (Al2O3), the respective proportions of which are, relative to the total mass of these three compounds:

Pr6O11: 1 wt % to 20 wt %,

NiO: 1 wt % to 20 wt %, and

Al2O3: 60 wt % to 98 wt %; and a means for passing a gas including at least carbon monoxide (CO) over the catalytic layer.

In some embodiments, the catalytic material has respective proportions, relative to the total mass of these three compounds, of:

Pr6O11: 5 wt % to 12 wt %,

NiO: 6 wt % to 12 wt %, and

Al2O3: 76 wt % to 88 wt %.

In some embodiments, the device comprises a fluidized bed comprising the catalytic layer.

In some embodiments, the device comprises at least one heat exchange tube immersed in the catalytic layer.

As the particular features, advantages and aims of this device are similar to those of the conversion method that is the subject of the invention, they are not repeated here.

BRIEF DESCRIPTION OF THE FIGURES

Other advantages, aims and features of the present invention will become apparent from the description that will follow, made, as a non-limiting example, with reference to the drawings included in an appendix, in which.

DESCRIPTION OF EXAMPLES OF REALIZATION OF THE INVENTION

The present description is given in a non-limiting way, each characteristic of an embodiment being able to be combined with any other characteristic of any other embodiment in an advantageous way.

All the contents are, in the description, expressed as a percentage by mass for the solids, and the contents of the gases are expressed as a percentage by volume in dry gas.

The catalytic material utilized by the method that is the subject of the invention comprises praseodymium oxide (Pr6O11) associated with nickel oxide (NiO) and alumina (Al2O3), the respective proportions of which are, relative to the total mass of these three compounds:

Pr6O11: 1 wt % to 20 wt %, preferably 3 wt % to 15 wt %, and, even more preferably, 5 wt % to 12 wt %;

NiO: 1 wt % to 20 wt %, preferably 3 wt % to 15 wt %, and, even more preferably, 6 wt % to 12 wt %; and Al2O3: 60 wt % to 98 wt %, preferably 70 wt % to 94 wt %, and, even more preferably, 76 wt % to 88 wt %.

Preferably, the alumina is mesoporous and preferably has a gamma structure. The mesoporosity range of the preferential alumina has a median diameter of the pores, determined by Hg intrusion porosimetry, of between 3 and 50 nm, and preferably between 5 and 25 nm.

The catalytic material's specific surface area SStel is preferably between 50 and 300 m²/g, and more preferably between 100 and 250 m²/g.

The inventors have discovered that the choice of this combination of compounds and the respective content of each of these elements, ($Pr_6O_{11}$, NiO and/or $Al_2O_3$) provide a good performance/durability/cost compromise when this catalytic material is used for converting carbon monoxide (CO) in a gas mixture rich in hydrogen (H2), possibly in the presence of carbon dioxide (CO2), into a gas mixture rich in methane (CH4), and, in particular, to conversions at low temperatures, for example below 300° C. on average in the reaction medium.

This conversion is also called methanation or the Sabatier reaction, and consists of hydrogenating the CO and/or CO2 to produce a gas containing CH4.

Preferably, the conversion is performed based on a gas mixture that mainly contains carbon monoxide (CO), carbon dioxide (CO2) and hydrogen (H2), in particular with a hydrogen (H2) content higher than that of the carbon monoxide (CO) and carbon dioxide (CO2).

The conversion can be performed effectively at an average temperature, in the reaction medium, below 300° C., unlike catalysts previously known.

Different methods can be used to prepare the catalytic material.

Figure 2:
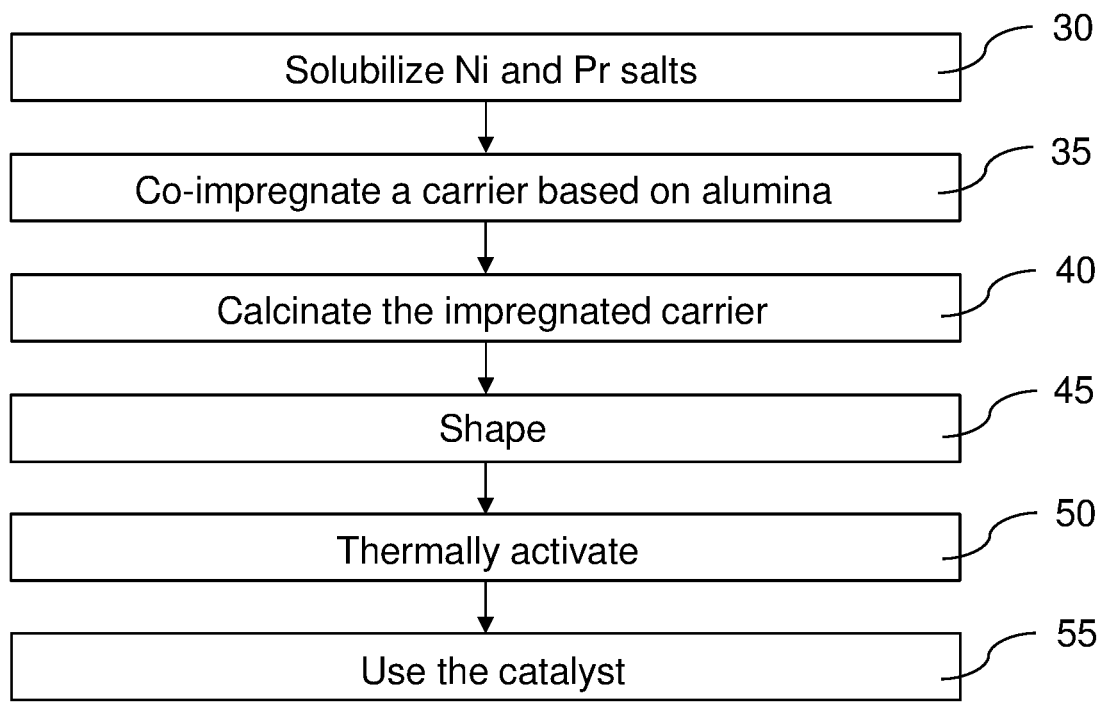
FIG. 2 represents, in the form of a logical diagram, a particular embodiment of the method of preparing the catalytic material that is the subject of the invention.

In some embodiments, the catalytic material production method comprises, as shown in FIG. 2:
a step 30 of the solubilization of salt precursors of nickel and praseodymium, separately or in a mixture;
a step 35 of the surface deposition of metal salts on a carrier based on alumina ($Al_2O_3$);
a step 40 of thermal decomposition in an atmosphere comprising oxygen and, possibly, of the dehydration of an alumina hydrate leading to an alumina in gamma or delta form; and
a step 50 of activating the material obtained by heat treatment in the presence of reducing agents.

The step 30 consists of solubilizing, separately or in a mixture, the base materials of the salt precursors of nickel and praseodymium. During the step 35, a surface deposition of these metal salts is performed on a carrier based on alumina, generally alumina ($Al_2O_3$) or boehmite-type alumina hydrate (AlOOH). During the step 40, a heat treatment is performed in an atmosphere comprising oxygen, for example in air or in oxygen, making it possible to decompose the metal precursors and obtain alumina in gamma or delta form when the carrier employed is initially boehmite-type alumina hydrate (AlOOH).

In the embodiments of the method described below, the surface deposition of the salt precursors of nickel and praseodymium is performed on a carrier comprising alumina, preferably already in gamma or delta form, or on a boehmite-type alumina hydrate carrier, which leads to an alumina in gamma or delta form when it is dehydrated during the heat treatment step.

In the case of thermal decomposition in air, this is performed in a temperature range of 300-800° C., preferably 400-600° C., and, even more preferably, 350-500° C., preferably for a length of time of between one hour and four hours.

During the step 45, a catalyst is formed based on the catalytic material obtained during the step 40. During the step 50, the catalyst is activated. This activation by heat treatment in the presence of reducing agents or by chemical treatment partially or fully transforms the nickel oxide into nickel. The step of activating the catalytic material is preferably performed in the presence of reducing agents, in a temperature range of 300-500° C. and preferably 400-500° C.

During the step 55, the catalyst is used by passing a gas including carbon monoxide (CO) and hydrogen (H2) over the activated catalytic material, possibly in the presence of carbon dioxide.

Figure 1:
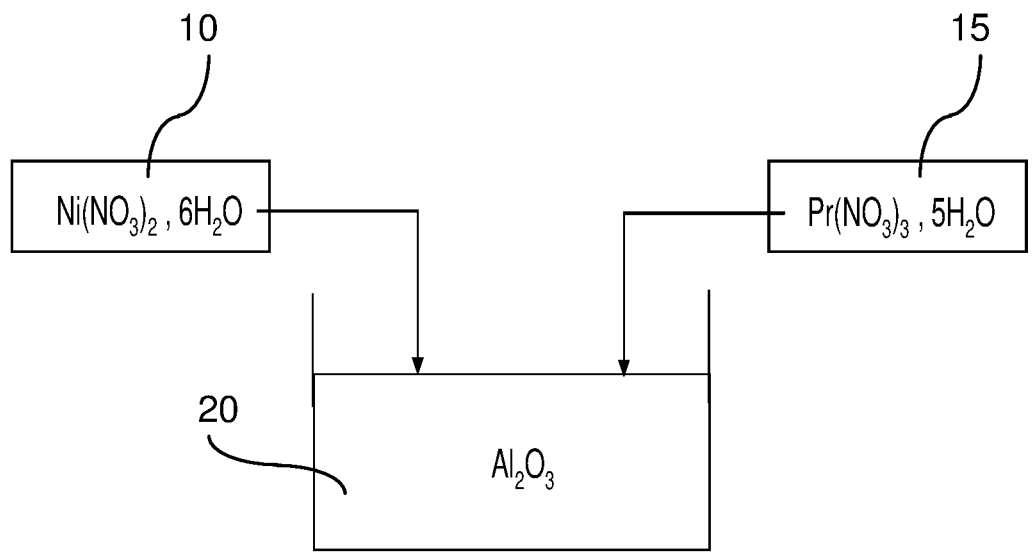
FIG. 1 is a block diagram of a particular production method of the catalytic material that is the subject of the invention.

A first method example comprises the co-impregnation of praseodymium salts 15 and nickel salt 10 on a carrier 20 (see FIG. 1), during a step 35 (see FIG. 2). The carrier is, for example a boehmite-type alumina hydrate, or alumina ($Al_2O_3$) crystallized in gamma or delta form. The salts used can be chlorides, nitrates, acetates, or sulfates.

Each of the above-mentioned Ni and Pr salts is solubilized simultaneously under agitation, in order to form a homogeneous solution (step 30) which is then put in contact with the carrier (step 35). The solution of these metal precursors is then absorbed in the porosity of the carrier.

For example, the nickel salt takes the hydrated form $Ni(NO_3)_2$, $6H_2O$, and the praseodymium salt takes the form $Pr(NO_3)_3$, $5H_2O$.

Such an impregnation can be performed:
"dry": the volume of prepared solution is therefore less than or equal to the volume that can be absorbed by the carrier; or
by excess solvent: in that case, a drying phase is necessary.

The impregnated carriers then undergo calcination (step 40) in order to thermally decompose the metal precursors, and form the Ni and Pr oxides. In the case where boehmite-type alumina hydrate is used, the calcination step transforms the alumina hydrate into alumina.

A second method example of the preparation of the catalytic material comprises successive impregnations of nickel salts then praseodymium salts, or praseodymium salts then nickel salts, on alumina or on boehmite-type alumina hydrate.

The selected metal salts of nickel and praseodymium are solubilized separately. The solution containing the salt of the first metal (nickel or praseodymium, respectively) is then impregnated on the carrier as described in the first method example, dry or by excess solvent.

A calcination step then makes it possible to decompose the metal precursor in order to form an intermediate product and possibly transform the alumina hydrate into alumina. The latter is then impregnated by the second solution containing the salt of the second metal (praseodymium or nickel, respectively) by again following the same steps.

A third method example of the preparation of the catalytic material comprises co-precipitation of the nitrate salts of praseodymium, nickel and alumina or boehmite-type alumina hydrate, also followed by thermal decomposition.

A fourth method example of the preparation of the catalytic material comprises atomization of a suspension containing salts of nickel, praseodymium and boehmite or alumina, followed by a step of calcination in air.

During the drying by atomization, the suspension is sprayed as fine droplets by means of an atomizer turbine, or by high pressure injection through nozzles, into a vertical cylindrical chamber swept by a flow of hot air. Evaporation of the water leads to the formation of a dry powder collected in the bottom portion of the equipment. This drying method makes it possible to form a catalytic material with a targeted particle size, dependent on the atomization parameters and the characteristics of the equipment.

In all the methods for the preparation of the catalytic material mentioned above, the oxide obtained from the calcination step (step 40) is activated in a reducing gas (CO, H2, NH3, etc.) that is pure or diluted with an inert gas (Ar, N2, He, etc.), following a suitable temperature profile, to transform all or part of the nickel oxide (NiO) into dispersed metallic Ni during a step 50.

With respect to the suitable profile, for example, the catalytic material is activated in a flow of a gas containing hydrogen during a temperature profile comprising increasing the ambient temperature to 400° C. with a ramp of 2° C./min, and a four-hour plateau at 400° C., preferably in the presence of reducing agents. More generally, the activation step is preferably performed in a temperature range of 300-500° C. and preferably 400-500° C.

The catalytic material in the strict sense can be in powdery form, in which the mean size of the grains varies from 1 to 100 μm. The catalytic material can be in different forms (step 45): powder, foam (metal or ceramic), coated on ceramic (cordierite, mullite, etc.) or metallic substrates, or ceramic filters, extruded with different geometries (single-lobe, three-lobe, etc.), beads, pellets, etc.

In the case of beads, for example spherical or oblong, preferably, their mean size is between 100 μm and 1 mm, preferably between 200 and 800 μm and, even more preferably, between 200 and 600 μm.

A step (step 55) of using the catalytic material comprises the conversion of carbon monoxide (CO) into methane, in the presence of hydrogen (H2), possibly in the presence of carbon dioxide (CO2).

Preferably, the gas to be converted comprises at least 5% CO (volume content in dry gas), more preferably at least 10% CO (volume content in dry gas) and, even more preferably, 15% CO (volume content in dry gas).

15% CO (volume content in dry gas) corresponds, for example, to the minimum CO content usually measured in a gas from steam gasification.

Figure 3:
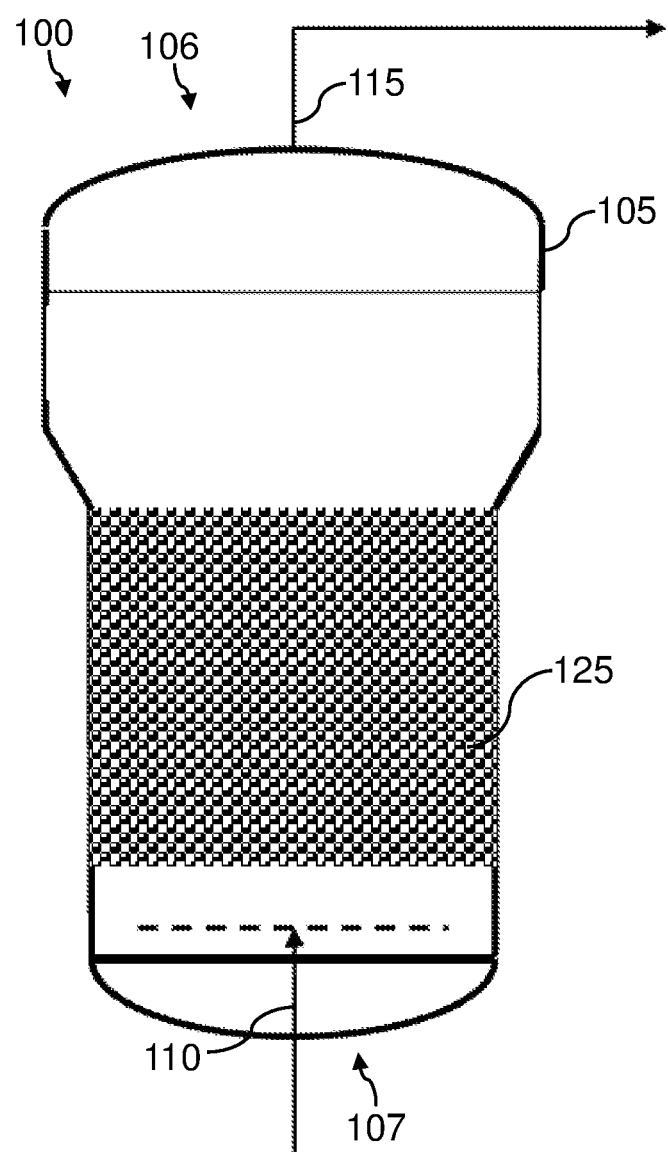
FIG. 3 represents a methanation unit utilizing the method that is the subject of the invention.

FIG. 3 shows a fluidized-bed reactor including the catalyst and leading to the conversion of a gas including at least carbon monoxide (CO) into methane (CH4), during the passage of this gas over the catalyst, i.e. the activated catalyst material.

For clarity, a fluidized bed enables a category of solids, here the catalyst, to be given certain properties of fluids, liquids or gases. It allows a strong interaction of catalyst particles and the gas traversing it. The principle of the fluidized bed is to inject a pressurized gas under a bed of solid particles. This gas lifts and disperses the solid particles. It enables more effective catalysts. This is known as a fluidized bed reactor (FBR).

The particle agitation and hydrodynamic mixing by flows of gaseous bubbles make the fluidized layers volumes in which the solid particles are vigorously agitated. There they can exchange heat and material very effectively, by direct contact, on a large specific surface, with the gas or with an immersed heat exchanger with a view to reusing or removing the heat produced by the gas conversion reaction when gas containing carbon monoxide is converted into methane. The fluidized layer therefore constitutes an open volume, practically isothermal, because of the high specific heat capacity by mass of the solids compared to that of the gas, and by their renewal on contact with the exchange surfaces.

FIG. 3, which is not to scale, shows a schematic view of an embodiment of the reactor 100. This reactor 100 comprises a chamber 105 having one longitudinal extremity 107, referred to as "lower", and one opposite longitudinal extremity 106, referred to as "upper". The chamber 105 is, for example, formed of a closed, sealed volume. The internal and/or external shape of the chamber 105 is not important for the present invention, provided the chamber is sealed. For example, the chamber 105 has a tubular shape, i.e. a cylindrical shape, which can be oblong as shown in FIG. 3.

The chamber 105 comprises, near the lower extremity 107, an inlet 110 of gas including carbon monoxide and hydrogen, and possibly carbon dioxide. The chamber 105 comprises, near the upper extremity 106, an outlet 115 for methane or for a gas rich in methane. An activated catalyst material 125, not consumable by the conversion reaction, forms a catalytic layer which is preferably a fluidized bed through which the gas coming from the inlet 110 passes.

The inlet, 110 is, for example, an injection nozzle, a nozzle, a perforated tube, a network of piping equipped with strainers. However, any fluid injector usually used in a reactor can be used to realize the inlet 110. The outlet 115 is, for example, an opening formed in the chamber 105 connected to a methane transport line.

In some variants, the reactor 100 comprises heat exchange tubes (not shown) immersed in the chamber 105 and traversed by a fluid having a temperature compatible with the nominal operating temperature inside the chamber 105 during the operation of the reactor 100. The fluid's temperature is lower than the interior of the chamber to enable the temperature of the reactor to be maintained by removing excess heat linked the exothermicity of the conversions utilized. Preferably, this removed excess heat is reused.

The average temperature of the reaction medium 125 and/or the output temperature of the catalytic layer 115 can be below 300° C. The exothermic reaction tends to raise the temperature and, in some preferred embodiments, the temperature of the reaction area is controlled to keep it, on average, below 300° C., which favors the thermodynamics while making the reaction possible. In this way a reaction with an increased yield is obtained.

Preferably, the pressure inside the chamber 105 is between one bar (atmospheric pressure) and 70 bar, preferably between 1 bar and 20 bar, and, more preferably, between 1 bar and 10 bar. These pressures optimize the conversion by minimizing the upstream compression costs.

Preferably, the fluidization/flow rate range is between one and sixteen times the minimum fluidization speed, preferably between two and eight times the minimum fluidization speed, which optimizes the heat exchange.

With respect to the source of the CO, CO2, or hydrogen, the reactor can be preceded by a pyrolysis unit for hydrocarbon materials (biomass, waste, carbon, etc.), a pyrogasification unit for hydrocarbon materials (biomass, waste, carbon, etc.), a gasification unit for hydrocarbon materials (biomass, waste, carbon, etc.), a Water-Gas-Shift unit, a Reverse Water-Gas-Shift unit, or a CO2/H2O co-electrolysis unit, as described in patent application EP 16757688.3, included here as reference. For clarity, Water-Gas-Shift (WGS) is a means for adjusting CO content, and Reverse Water-Gas-Shift is a means for producing CO at a high temperature from a H2+CO2=CO+H2O mixture (inverse of the Water-Gas-Shift (WGS) reaction).

As an example, the catalyst utilized by the method of the invention offers activity at 250° C., higher than commercially available technology (Reference technology having a composition of 50% nickel on alumina, with no praseodymium), as the following table shows:

Test conditions: temperature 250° C., atmospheric pressure, hourly volumetric flow rate=10,000 h-1.

Composition of the gas flow: 12% CO, 8% CO2, 70% H2, 5% H2O, 5% CH4.

|  | Catalyst of the invention | Commercially available catalyst |
| --- | --- | --- |
| CO conversion | 95% | 25% |
| CO2 conversion | 7.5% | 0% |

To be active in methanation, the catalyst must undergo a reduction treatment that modifies the oxidation state of the Ni and Pr. In the example presented here, the catalytic material has undergone a reduction treatment in a gas flow containing hydrogen at 450° C. during a four-hour period.

It is noted that the catalyst formed with the catalytic material is at least as effective as the commercially available catalyst for average temperatures, in the reaction medium, higher than 300° C.

The catalytic material therefore has a broader operating temperature range, 220-400° C., preferably 250-350° C.

In this comparative test, the catalyst utilized by the method of the invention is the catalyst of its most preferred embodiments.

The conversion rates are defined by the ratios ([CO or CO2]input—[CO or CO2]output)/([CO or CO2]input).

The invention therefore applies particularly well to the field of the conversion of carbon monoxide (CO), possibly in the presence of carbon dioxide (CO2) and a gas mixture rich in hydrogen, into a mixture rich in methane (CH4), and, in particular, to conversions at low temperatures.

The invention claimed is:

1. A method for converting a gas into methane ($CH_4$), that comprises:
   a step of activating a catalytic material consisting of praseodymium oxide ($Pr_6O_{11}$) associated with nickel oxide (NiO) and alumina ($Al_2O_3$), the respective proportions of which are, relative to the total mass of these three compounds:
   $Pr_6O_{11}$: 1 wt % to 20 wt %,
   NiO: 1 wt % to 20 wt %, and
   $Al_2O_3$: 60 wt % to 98 wt %; and
   a step of passing a gas including at least carbon monoxide (CO) over the activated catalytic material.

2. The method according to claim 1, wherein the gas passing over the activated catalytic material also comprises carbon dioxide ($CO_2$).

3. The method according to claim 1, wherein the proportion of carbon monoxide in the gas reaching the activated catalytic material is higher than five percent by volume in dry gas.

4. The method according to claim 1, wherein, during the gas passage step, a gas mixture is passed that mainly contains CO, $CO_2$ and $H_2$, with an $H_2$ content higher than that of CO and $CO_2$.

5. The method according to claim 1, wherein, during the gas passage step, the mean temperature of the catalytic layer is below 300° C.

6. The method according to claim 1, which further comprises a step of shaping the catalytic material into beads with a mean size of between 100 and 1000 μm.

7. The method according to claim 1, wherein before the activation step, the catalytic material has respective proportions, relative to the total mass of these three compounds, of:
$Pr_6O_{11}$: 3 wt % to 15 wt %,
NiO: 3 wt % to 15 wt %, and
$Al_2O_3$: 70 wt % to 94 wt %.

8. The method according to claim 1, wherein the alumina has a mesoporosity corresponding to a median diameter of the pores, determined by Hg intrusion porosimetry, of between 3 and 50 nm.

9. The method according to claim 1, wherein the alumina has a gamma structure.

10. The method according to claim 1, wherein the catalytic material's specific surface area SStel is between 50 and 300 $m^2/g$.

11. The method according to claim 1, wherein the catalytic material's specific surface area SStel is between 100 and 250 $m^2/g$.

12. The method according to claim 1, wherein the step of activating the catalytic material comprises heat treatment in the presence of reducing agents.

13. The method according to claim 2, wherein the step of activating the catalytic material in the presence of reducing agents is performed in a temperature range of 300-500° C.

14. The method according to claim 1, which further comprises
   a step of the solubilization of salt precursors of nickel and praseodymium, separately or in a mixture;
   a step of the surface deposition of metal salts on a carrier based on alumina ($Al_2O_3$); and
   a step of thermal decomposition in an atmosphere comprising oxygen and in a temperature range of 350-500° C., for a period of between one hour and four hours.

15. The method according to claim 1, which further comprises, before the gas passage step, a step of constituting the gas comprising at least one of the following steps:
   pyrolysis of hydrocarbon materials;
   pyro-gasification of hydrocarbon materials;
   gasification of hydrocarbon materials;
   co-electrolysis of $CO_2/H_2O$;
   water-Gas-Shift; and
   reverse Water-Gas-Shift.

16. The method according to claim 1, wherein, during the step of passing the gas over the catalytic material, the gas goes through a catalytic layer of activated catalytic material.

17. The method according to claim 16, wherein, during the step of passing the gas over the catalytic material, the gas goes through a fluidized bed of activated catalytic material.

18. The method according to claim 16, which further comprises a step of cooling the catalytic layer by at least one heat exchange tube immersed in the catalytic layer.

19. The method according to claim 2, wherein the step of activating the catalytic material in the presence of reducing agents is performed in a temperature range of 400-500° C.

* * * * *